US007981061B2

(12) United States Patent
Kusuura

(10) Patent No.: US 7,981,061 B2
(45) Date of Patent: Jul. 19, 2011

(54) POWER APPARATUS, POWER SYSTEM, AND POWER CONTROL METHOD

(75) Inventor: Takahisa Kusuura, Kawasaki (JP)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 12/778,352

(22) Filed: May 12, 2010

(65) Prior Publication Data

US 2011/0144547 A1 Jun. 16, 2011

(30) Foreign Application Priority Data

Dec. 14, 2009 (JP) ................................. 2009-283043

(51) Int. Cl.
*A61F 5/00* (2006.01)
*A61H 1/00* (2006.01)

(52) U.S. Cl. ................................ 601/5; 601/23; 601/33

(58) Field of Classification Search ................ 601/5, 23, 601/24, 33, 84, 86, 87; 602/5, 16, 20, 23
See application file for complete search history.

(56) References Cited

U.S. PATENT DOCUMENTS 6,966,882 B2 * 11/2005 Horst ................................ 601/5
7,445,606 B2 * 11/2008 Rastegar et al. .................. 601/5
7,537,573 B2 * 5/2009 Horst ................................ 601/5

FOREIGN PATENT DOCUMENTS

JP 06-086407 3/1994
JP 2007-054086 3/2007
JP 2008-061405 3/2008

OTHER PUBLICATIONS

Office Action for JP 2009-283043 mailed Mar. 5, 2010 (with English translation).
"Robot Watch," Internet URL: http://robot.watch.impress.co.jp/cda/news/2008/11/07/1427.html, searched on Nov. 24, 2009, 20 pages.

* cited by examiner

*Primary Examiner* — Quang D Thanh
(74) *Attorney, Agent, or Firm* — Foley & Lardner LLP

(57) ABSTRACT

A power apparatus comprising includes: a moving section that moves in accordance with an action of a body part; a motor that outputs, during action of the body part in a first action direction, power to the moving section so as to cause the moving section to move in the first action direction and that recovers, during action of the body part in a second action direction, power generated by the movement of the moving section in the second action direction; and a capacitor that stores regenerative electric power generated by the recovery of the power and that supplies the stored regenerative electric power to the motor when the motor outputs the power to the moving section.

8 Claims, 11 Drawing Sheets

| OPERATION/ RECOVERY | CAPACITOR VOLTAGE | BATTERY | CAPACITOR | LOAD |
|---|---|---|---|---|
| OPERATION (1) | SMALLER THAN PREDETERMINED VALUE | ON | OFF | OFF |
| OPERATION (2) | PREDETERMINED VALUE OR GREATER | OFF | ON | OFF |
| RECOVERY (1) | SMALLER THAN PREDETERMINED VALUE | OFF | ON | OFF |
| RECOVERY (2) | PREDETERMINED VALUE OR GREATER | OFF | OFF | ON |

POWER APPARATUS, POWER SYSTEM, AND POWER CONTROL METHOD

CROSS REFERENCE TO RELATED APPLICATION

This application claims the benefit of Japanese Application No. 2009-283043 filed on Dec. 14, 2009, which is incorporated herein by reference.

BACKGROUND OF THE INVENTION

1. Field of the Invention

The present disclosure relates to a power apparatus, a power system, and a power control method.

2. Description of the Related Art

In recent years, power apparatuses, such as operation aiding equipment for aiding/acting for operations of physically-disabled people, the elderly, workers, and so on and robot suits for augmenting human muscle power have been developed (e.g., refer to "Robot Watch", Internet URL: http://robot.watch.impress.co.jp/cda/news/2008/11/07/1427.html, searched on Nov. 24, 2009).

In terms of the weights of the apparatuses, the known power apparatuses are typically equipped with lightweight, small-capacity batteries. Examples of the batteries include lithium-ion batteries and nickel-hydrogen batteries.

However, since the operating time of small-capacity batteries provided in the known power apparatuses is short (e.g., one to three hours), the users often have to carry backup batteries with them. This is burdensome and inconvenient for the users.

Since the batteries used for the know power apparatuses are high in the internal resistance and are short in the life cycle, it has been practically difficult to charge the batteries with an energy source that temporarily generate electric power at high frequency.

SUMMARY OF THE INVENTION

Accordingly, it is desired to provide a power apparatus, a power system, and a power control method which are capable of extending the operating time while using currently available small-capacity batteries.

A power apparatus according to the present disclosure includes: a moving section that moves in accordance with an action of a body part; a motor that outputs, during action of the body part in a first action direction, power to the moving section so as to cause the moving section to move in the first action direction and that recovers, during action of the body part in a second action direction, power generated by the movement of the moving section in the second action direction; and a capacitor that stores regenerative electric power generated by the recovery of the power and that supplies the stored regenerative electric power to the motor when the motor outputs the power to the moving section.

The power apparatus according to the present disclosure may further include a battery that supplies battery electric power to the motor when the motor outputs the power to the moving section.

The power apparatus according to the present disclosure may further include a controlling section that controls switching between a first mode in which the motor outputs the power to the moving section and a second mode in which the power generated by the movement of the moving section is recovered.

In the first mode, the controlling section may perform control so as to supply the regenerative electric power from the capacitor to the motor when the regenerative electric power stored in the capacitor is greater than or equal to a predetermined value and so as to supply the battery electric power from the battery to the motor when the regenerative electric power stored in the capacitor is smaller than the predetermined value.

In the second mode, the controlling section may perform control so as to supply the regenerative electric power to the capacitor when a voltage value of the capacitor is not a maximum value and so as to supply the regenerative electric power to a load when the voltage value of the capacitor is the maximum value.

When the moving section is not moving and the capacitor stores the regenerative electric power, the controlling section may supply the regenerative electric power from the capacitor to the battery.

The power apparatus according to the present disclosure may further include an acceleration sensor that measures acceleration of the action of the body part. When the measured acceleration contains a component in a direction opposite to a direction of gravity, the controlling section switches a mode to the first mode to perform control, and when the measured acceleration contains a component in the direction of gravity, the controlling section switches a mode to the second mode to perform control.

The power apparatus according to the present disclosure may further include an electromyograph that measures a myoelectric potential of the body part. In the second mode, the controlling section controls a recovery load of the motor in accordance with the measured myoelectric potential.

The power apparatus according to the present disclosure may further include an electromyograph that measures a myoelectric potential of the body part. When the measured myoelectric potential is a potential corresponding to an action in the first action direction, the controlling section switches a mode to the first mode to perform control. When the measured myoelectric potential is a potential corresponding to an action in the second action direction, the controlling section switches a mode to the second mode to perform control.

A power system according to the present disclosure includes a first power apparatus and a second power apparatus. The first power apparatus has a first moving section that moves in accordance with a direction of an action of a body part, a motor that recovers power generated by the movement of the first moving section during the action of the body part, and an electric-power transmitting section that transmits regenerative electric power generated by the recovery of the power. The second power apparatus has a second moving section that moves in accordance with a direction of an action of a body part, an electric-power receiving section that receives the transmitted regenerative electric power, and a motor that outputs power to the second moving section, the regenerative electric power being supplied to the motor during the action of the body part. At least one of the first power apparatus and the second power apparatus includes a capacitor that stores the regenerative electric power.

A power control method according to the present disclosure is a power control method for controlling the above-described power apparatus. The power control method includes: causing the motor to receive, during action of the body part in the first action direction, the regenerative electric power supplied from the capacitor and to output the power to the moving section; and causing the motor to recover, during action of the body part in the second action direction, the power generated by movement of the moving section in the second direction and causing the capacitor to store regenerative electric power generated by the recovery of the power.

DESCRIPTION OF THE PREFERRED EMBODIMENTS

Figure 1:
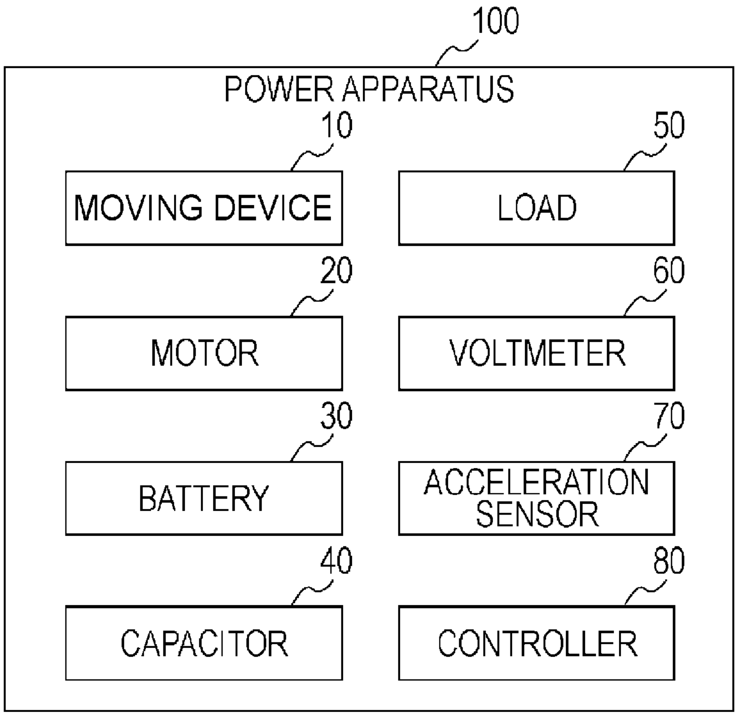
FIG. 1 is a block diagram showing a typical configuration of a power apparatus according to a present embodiment.

A preferred embodiment for embodying the present disclosure will be described below with reference to the accompanying drawings. The sizes, positional relationships, and so on of elements illustrated in the drawings may be exaggerated for clarity of description.

Figure 2A:
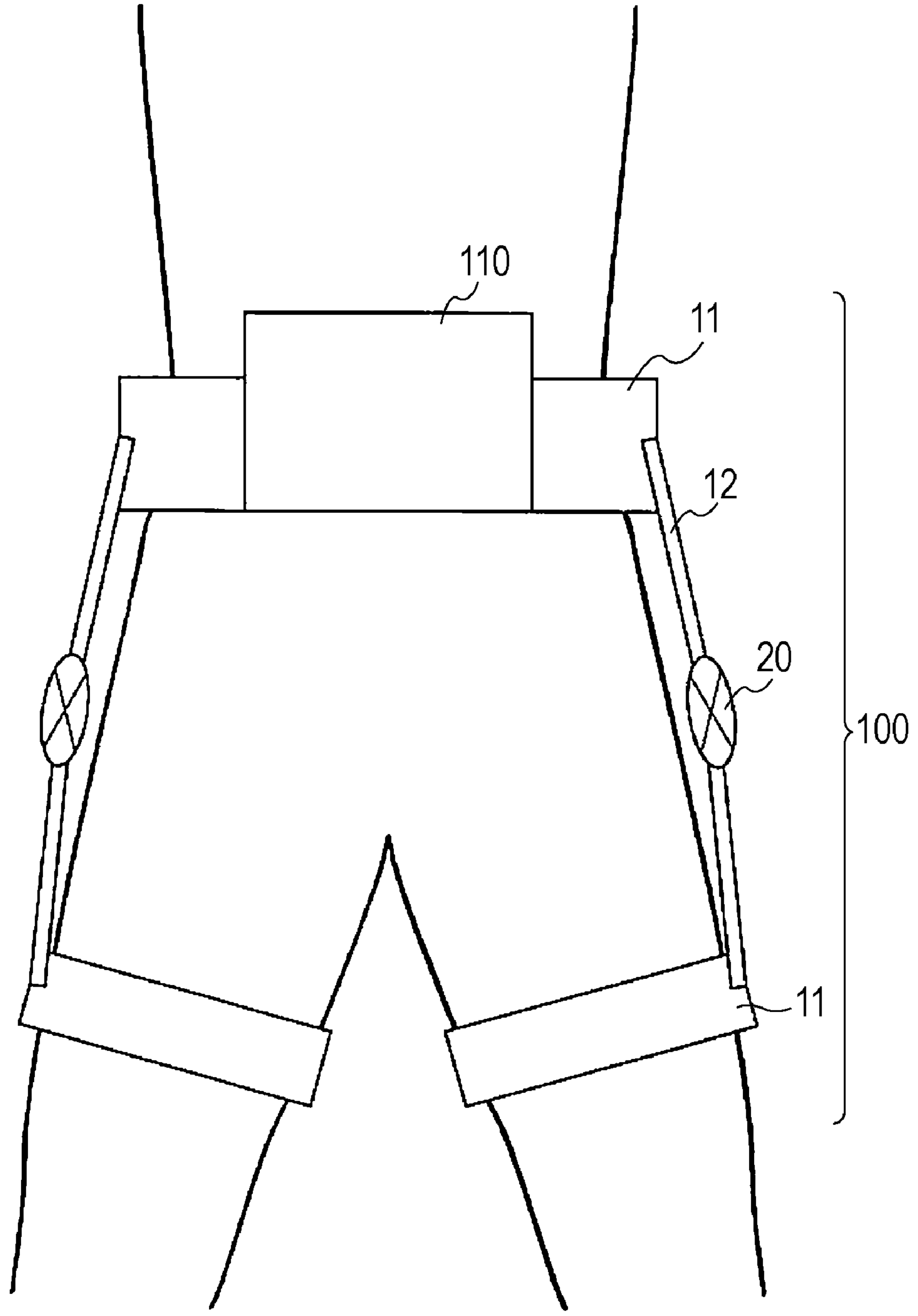
FIGS. 2A to 2C are schematic external views of the power apparatus according to the present embodiment.
Figure 2B:
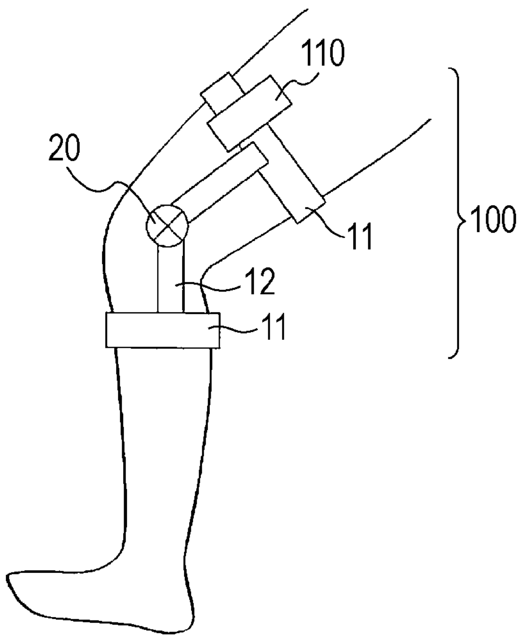
Figure 2C:
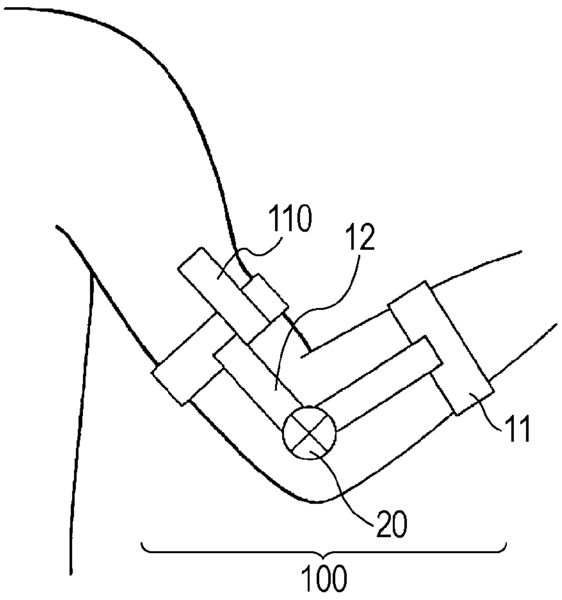

FIG. 1 is a block diagram showing a schematic configuration of a power apparatus 100 according to an embodiment. FIGS. 2A to 2C are schematic external views of the power apparatus 100 according to the present embodiment.

The power apparatus 100 is an apparatus attached to a part of a human body to support human operations. As shown in FIG. 1, the power apparatus 100 includes a moving device 10, a motor 20, a battery 30, a capacitor 40, a load 50, a voltmeter 60, an acceleration sensor 70, and a controller 80. The power apparatus 100 may have an accommodating unit 110 (see FIGS. 2A to 2C) that accommodates the battery 30, the capacitor 40, the load 50, the voltmeter 60, the acceleration sensor 70, and the controller 80.

The moving device 10 configured to move in accordance with an action of a body part (e.g., the lumbar part, elbows, or knees) that performs a flexing action. The moving device 10 has supporting sections 11 and linking sections 12. The supporting sections 11 are attached to the body so as to sandwich a body part for performing a flexing action. Each linking section 12 has a rotation mechanism for rotation in the vicinity of the body part for performing the flexing action.

For example, when the moving device 10 moves in accordance with an action of the lumbar part (which is an example of the body part for performing the flexing action), the linking sections 12 move rotatably in accordance with sitting-down and standing-up actions of the human part, with the supporting sections 11 being attached to the waist and both thighs, as shown in FIG. 2A. The moving device 10 is not limited to a case in which it moves in accordance with an action of the lumbar part. For example, the moving device 10 may move in accordance with an action of a knee, as shown in FIG. 2B, or may move in accordance with an action of an elbow, as shown in FIG. 2C. Since the structure and the material of moving device, such as known operation aiding equipment or a robot suit, can essentially be employed as the structure and the material of the moving device 10, a detailed description thereof is not given herein.

When the body part performs an action in a first action direction, the motor 20 outputs power to the rotation mechanism of the moving device 10 so as to cause the moving device 10 to move in the first action direction. When the body part performs an action in a second action direction, the motor 20 recovers power generated by the movement of the moving device 10 in the second action direction. For example, as shown in FIG. 2A, when the moving device 10 moves in accordance with an action of the lumbar part (which is an example of the body part for performing the flexing action), the first action direction can be regarded as a direction in which the action of standing up is performed (i.e., a direction in which the linking sections 12 is opened with the rotation mechanism being the center thereof) and the second action direction can be regarded as a direction in which the action of sitting down is performed (i.e., a direction in which the linking sections 12 are closed with the rotation mechanism being the center thereof). In particular, setting the second action direction to a direction in which potential energy is collectable makes it possible to efficiently recover power. As shown in FIGS. 2A to 2C, the motor 20 is disposed so that it can supply power for rotating the rotation mechanism of the moving device 10. Since the motor 20 may be implemented by a typical motor (e.g., a DC (direct current) motor or a brushless DC motor), a detailed description thereof is not given herein.

The battery 30 is an electric power source for supplying battery electric power to the motor 20 when the motor 20 outputs power to the moving device 10. The battery 30 may be, for example, a rechargeable battery, such as a lithium-ion battery or a nickel hydrogen battery.

The capacitor 40 serves as an electric power source that stores regenerative electric power generated by recovery of the power of the motor 20 and that supplies the stored regenerative electric power to the motor 20 when the motor 20 outputs power to the moving device 10. The capacitor 40 may be implemented by a capacitor that is low in internal resistance and is chargeable with electric power at high frequency. One example of the capacitor 40 is an electric double-layer capacitor (an ultracapacitor). The capacitor 40 can be implemented by not only the ultracapacitor but also a capacitor that is chargeable with regenerative electric power generated by recovery of motor power.

The load 50 is, for example, a resistor, and is capable of consuming regenerative electric power generated by recovery of the power of the motor 20. When the capacitor 40 for the regenerative electric power is fully charged, the regenerative electric power is supplied to the load 50.

The voltmeter 60 measures a voltage value of the capacitor 40. The voltmeter 60 sends information of the measured voltage value to the controller 80. Since the voltmeter 60 can be implemented by a known voltmeter, a detailed description thereof is not given herein.

The acceleration sensor 70 measures acceleration of an action of the body part. The acceleration sensor 70 sends the value of the measured acceleration component to the controller 80. The acceleration sensor 70 can be implemented by a three-axis acceleration sensor that measures acceleration in three-dimensional axis directions (i.e., an x-axis direction, a y-axis direction, and a z-axis direction). The acceleration sensor 70, however, is not limited to the three-axial acceleration sensor and may also be implemented by, for example, a single-axis acceleration sensor or a two-axis acceleration sensor. Since the acceleration sensor 70 can be implemented by a typical acceleration sensor, a detailed description thereof is not given herein.

The controller 80 serves as controlling device configured to control the entire power apparatus 100. More specifically, the controller 80 obtains the capacitor voltage value sent from the voltmeter 60 and obtains the body-portion acceleration value sent from the acceleration sensor 70. Further, on the basis of the voltage value and the acceleration value, the controller 80 controls switching between an operation mode (a first mode) in which the motor 20 outputs power to the moving device 10 and a recovery mode (a second mode) in which power generated by movement of the moving device 10 is recovered. The controller 80 can be realized using, for example, a typical microchip.

Figures 3, 4A:
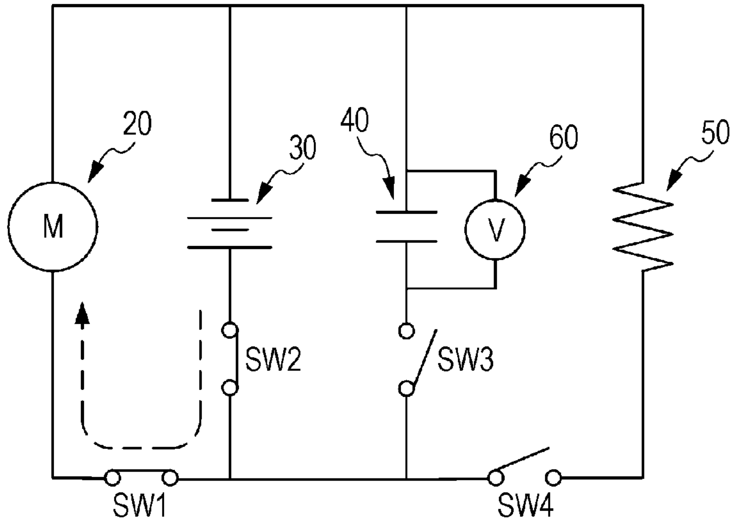
FIG. 3 shows relationships of a capacitor voltage, a battery, a capacitor, and a load in an operation mode and recovery mode of the power apparatus according to the present embodiment.
FIGS. 4A to 4E are diagrams illustrating a power control method for the power apparatus according to the present embodiment.

The operation mode and the recovery mode in the present embodiment will now be described in detail with reference to FIGS. 3 and 4A to 4E. FIG. 3 shows relationships of a capacitor voltage value, the battery 30, the capacitor 40, and the load 50 in each mode. FIGS. 4A to 4E are diagrams showing model circuits in respective modes to explain a power control method according to the embodiment. Since FIGS. 4A to 4E illustrate circuit elements needed to explain the power control method according to the present embodiment, another circuit element can be added thereto, as required, within a scope apparent to those skilled in the art.

The operation mode is a mode in which the motor 20 outputs power to the moving device 10, and includes a first operation mode and a second operation mode. In the first operation mode, when the voltage value of the capacitor 40 is smaller than a predetermined value, battery electric power is supplied from the battery 30 to the motor 20. In the second operation mode, when the voltage value of the capacitor 40 is greater than or equal to the predetermined value, regenerative electric power is supplied from the capacitor 40 to the motor 20. The predetermined value for the voltage value of the capacitor 40 may be, for example, a voltage value when electric charge of 80% or more of the capacity of the capacitor 40 is stored. The predetermined value, however, can be arbitrarily set depending on, for example, the application of the power apparatus 100.

In the first operation mode, as shown in FIGS. 3 and 4A, the controller 80 performs switching so as to turn on switches SW1 and SW2, which couple the motor 20 and the battery 30, in order to supply the battery electric power from the battery 30 to the motor 20 and so as to turn off switches SW3 and SW4, which couple the battery 30 with the capacitor 40 and the load 50, in order to prevent the battery electric power from being supplied to the capacitor 40 and the load 50.

Figure 4B:
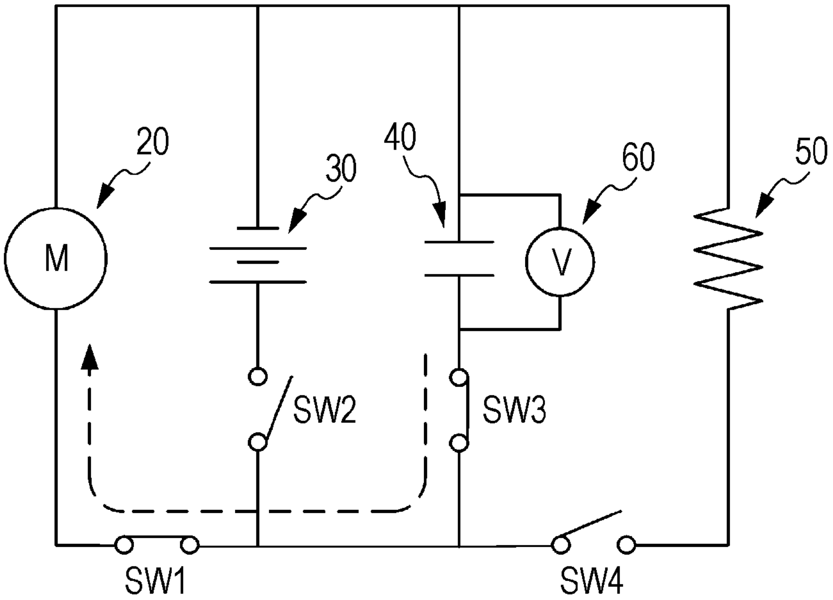

In the second operation mode, as shown in FIGS. 3 and 4B, the controller 80 performs switching so as to turn on the switches SW1 and SW3, which couple the motor 20 and the capacitor 40, in order to supply the charged regenerative electric power from the capacitor 40 to the motor 20 and so as to turn off the switches SW2 and SW4, which couple the capacitor 40 with the battery 30 and the load 50, in order to prevent the regenerative electric power stored in the capacitor 40 from being supplied to the battery 30 and the load 50.

The recovery mode is a mode in which power generated by movement of the moving device 10 is recovered, and includes a first recovery mode and a second recovery mode. In the first recovery mode, when the capacitor voltage value (capacitance) of the capacitor 40 is smaller than a predetermined value, the regenerative electric power generated by recovery of the power is supplied to the capacitor 40. In the second recovery mode, when the capacitor voltage value (capacitance) of the capacitor 40 is greater than or equal to the predetermined value, the regenerative electric power generated by recovery of the power is supplied to the load 50.

Figure 4C:
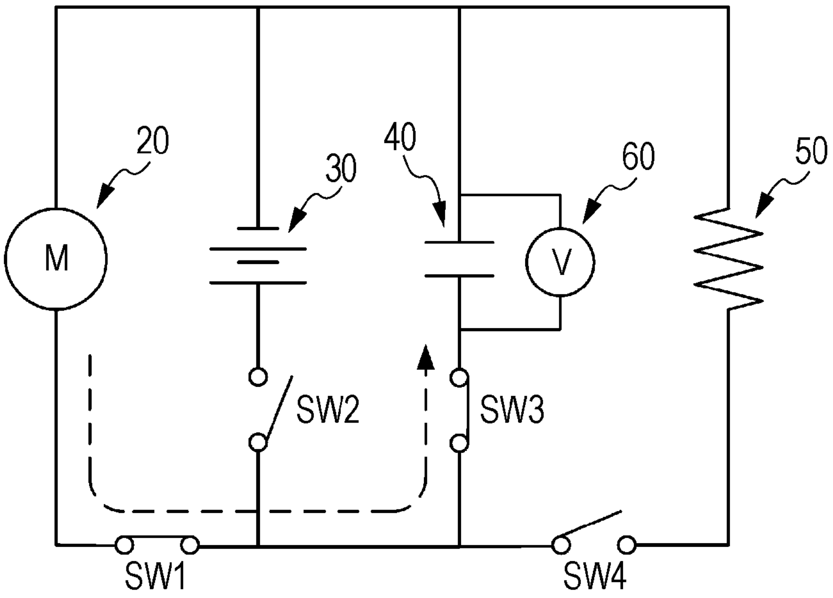

In the first recovery mode, as shown in FIGS. 3 and 4C, the controller 80 performs switching so as to turn on the switches SW1 and SW3, which couple the motor 20 and the capacitor 40, in order to supply the regenerative electric power, generated by recovery of the power of the motor 20, to the capacitor 40 and so as to turn off the switches SW2 and SW4, which couple the motor 20 with the battery 30 and the load 50, in order to prevent the regenerative electric power from being supplied to the battery 30 and the load 50.

Figure 4D:
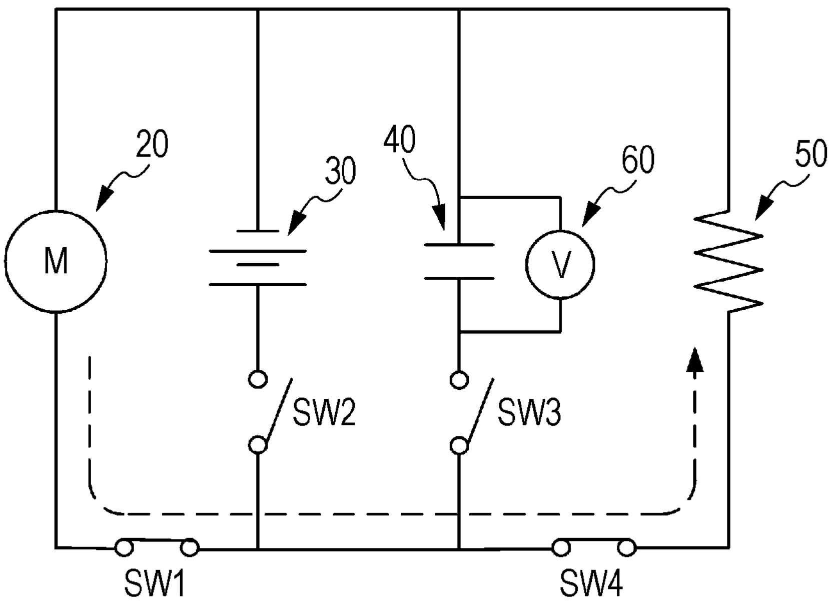

In the second recovery mode, as shown in FIGS. 3 and 4D, when the capacitor voltage (capacitance) is full, the controller 80 performs switching so as to turn on the switches SW1 and SW4, which couple the motor 20 and the load 50, in order to supply the regenerative electric power, generated by recovery of the power of the motor 20, to the load 50 and so as to turn off the switches SW2 and SW3, which couple the motor 20 with the battery 30 and the capacitor 40, in order to prevent the regenerative electric power from being supplied to the battery 30 and the capacitor 40.

Figure 4E:
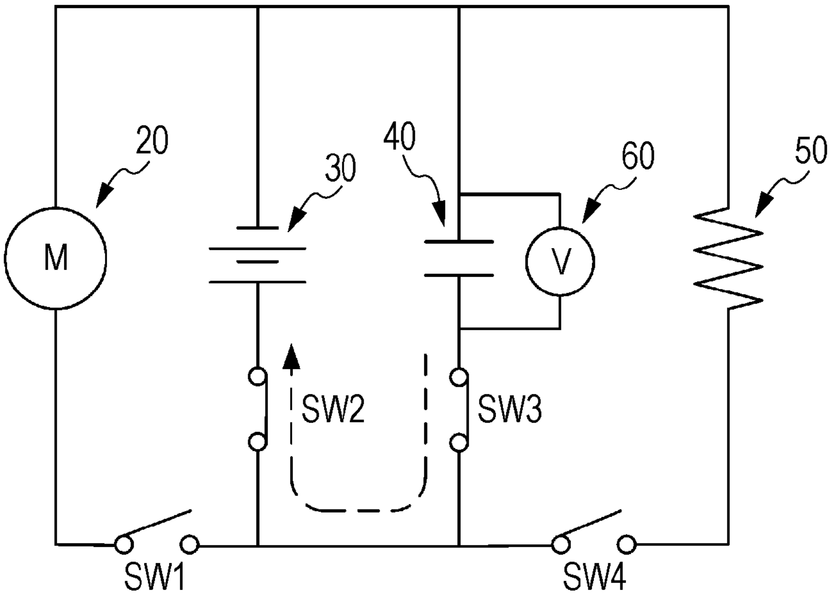

In a mode other than those described above, when the capacitor 40 is charged with a certain amount of regenerative electric power or more and the moving device 10 is not moving (i.e., when the motor 20 is stationary), the controller 80 may perform switching so as to turn on the switches SW2 and SW3, which couple the battery 30 and the capacitor 40, in order to supply the regenerative electric power, stored in the capacitor 40, to the battery 30 and so as turn off the switches SW1 and SW4, which couple the capacitor 40 with the motor 20 and the load 50, as shown in FIG. 4E. Supplying the regenerative electric power, stored in the capacitor 40, to the battery 30 makes it possible to increase the battery operating period. An electric-power converter circuit (e.g., a DC-DC converter) may be provided between the battery 30 and the capacitor 40, as needed, so as to allow for adjustment of electric power supplied from the capacitor 40 to the battery 30.

Figure 5A:
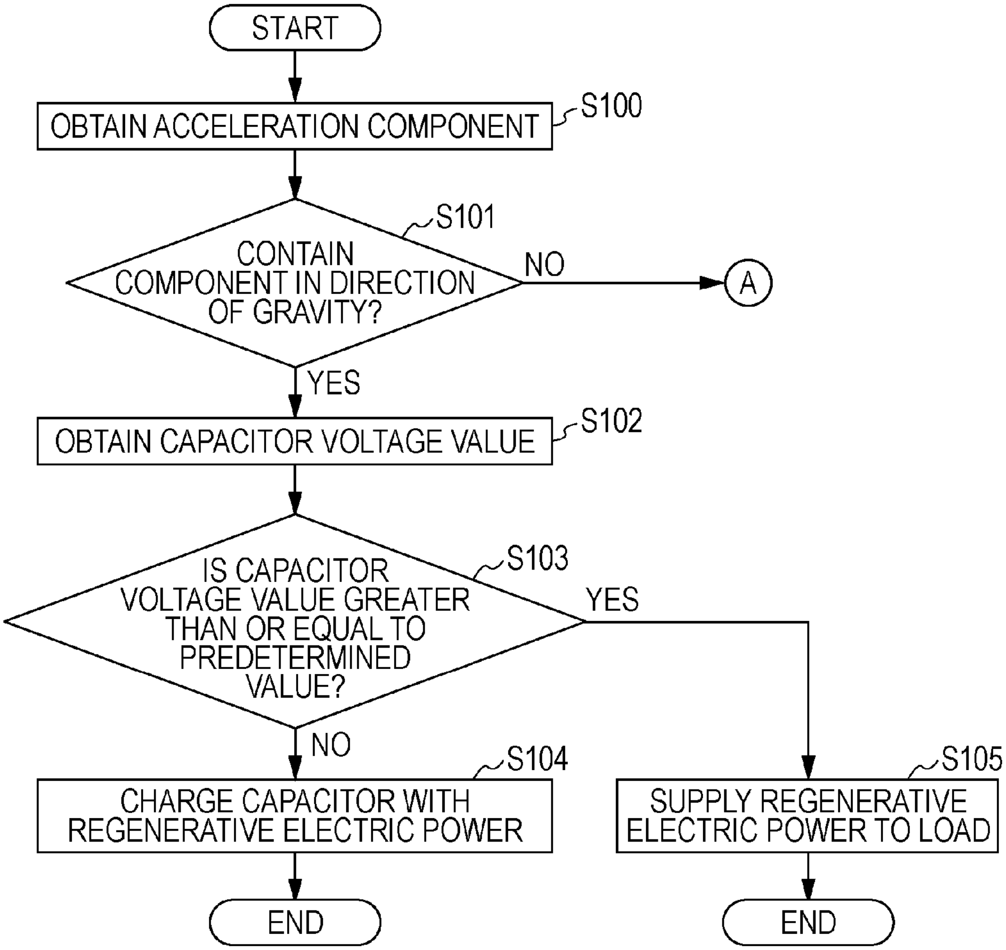
FIGS. 5A and 5B are flowcharts illustrating a power control method for the power apparatus according to the present embodiment.
Figure 5B:
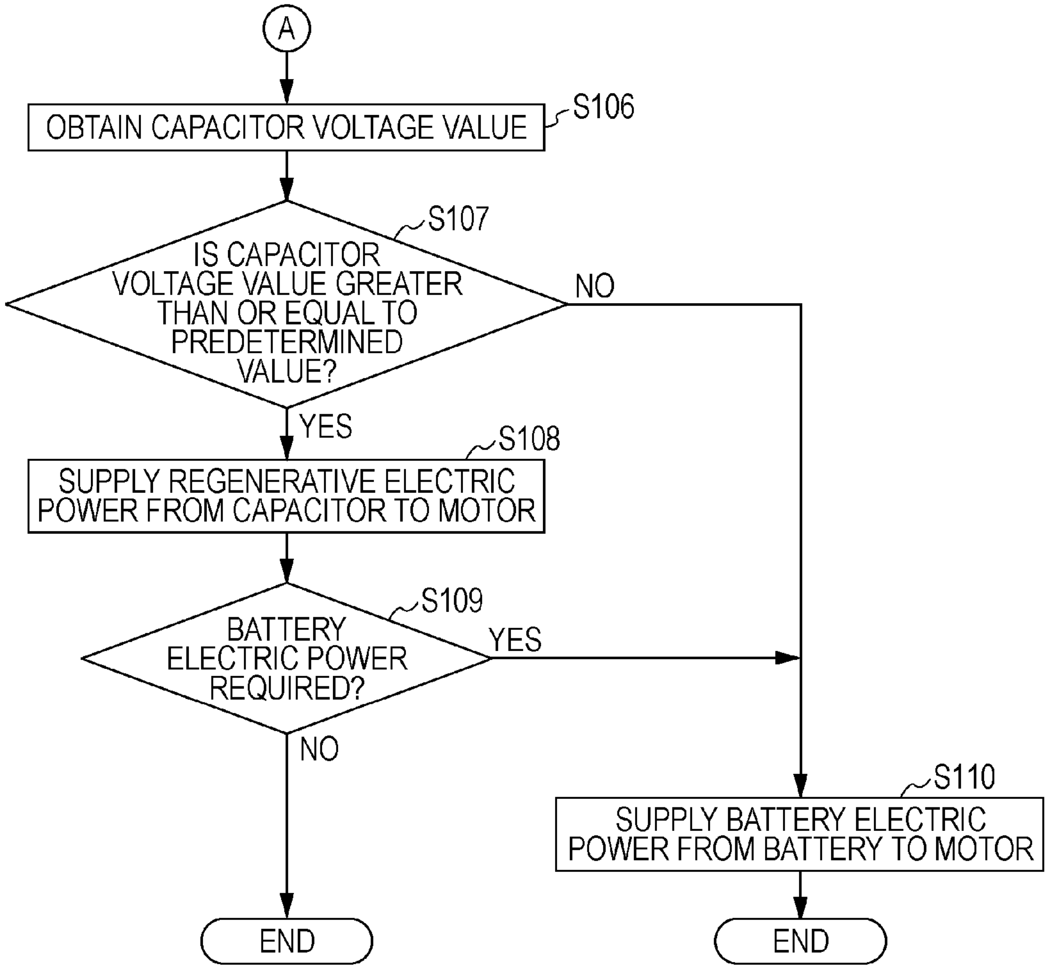
Figure 6:
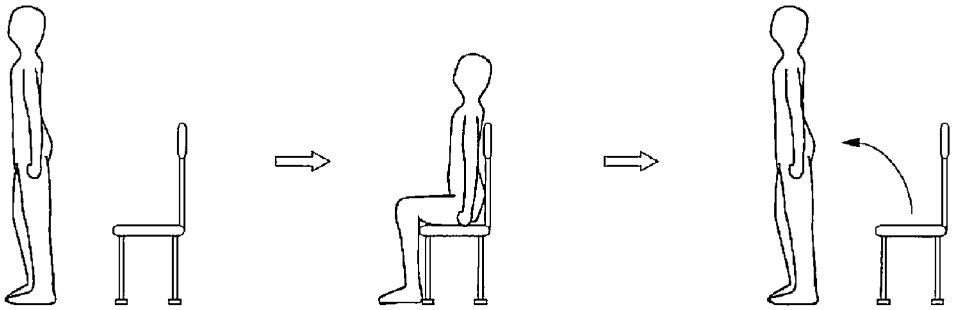
FIG. 6 shows one example of use of the power apparatus according to the present embodiment.

The power control method, executed using the power apparatus 100, according to the present embodiment will be described below with reference to flowcharts shown in FIGS. 5A and 5B. One example of the power control method will be described below in conjunction with a case in which a body part to which the power apparatus 100 is attached is a lumbar part (see FIG. 2A) and the user performs an action of standing up and an action of sitting down as shown in FIG. 6. Processing steps illustrated in the flowcharts may be executed in parallel or in an arbitrarily order modified to the extent that does not cause inconsistency in the contents of the processing.

First, in step S100, the controller 80 obtains an acceleration component value of the body part from the acceleration sensor 70 provided in the vicinity of the body part. When the obtained acceleration component value contains a component in the direction of gravity (Yes in step S101), the controller 80 executes processing in step S102. On the other hand, when the obtained acceleration component value does not contain a component in the direction of gravity (No in step S101), the controller 80 executes processing in step S107. For example, acceleration component values when the user performs an action of standing up and an action of sitting down may be pre-measured, so as to allow the recovery mode and the operation mode to be switched when the actually obtained acceleration value matches a predetermined range of the pre-measured acceleration component values. In such a case, the controller 80 can perform the switching not only on the basis of the component in the direction of gravity but also in response to the user's action.

When it is determined from the obtained acceleration value that the user performs an action of sitting down, the process proceeds to step S102 in which the controller 80 switches the mode to the recovery mode to obtain a capacitor voltage value from the voltmeter 60, which measures the voltage of the capacitor 40.

When the obtained capacitor voltage value is smaller than the predetermined value (No in step S103), the process proceeds to step S104 in which the controller 80 performs switching so as to supply the regenerative electric power to the capacitor 40 and performs control. For example, the controller 80 couples the motor 20 and the capacitor 40 in order to supply the regenerative electric power, generated by recovery of the power, to the capacitor 40 and decouples the motor 20 from the battery 30 and the load 50 in order to prevent the regenerative electric power from being supplied to the battery 30 and the load 50.

When the obtained capacitor voltage value is greater than or equal to the predetermined value (Yes in step S103), the process proceeds to step S105 in which the controller 80 performs switching so as to supply the regenerative electric power to the load 50. For example, the controller 80 couples the motor 20 and the load 50 in order to supply the regenerative electric power, generated by recovery of the power, to the load 50, and decouples the motor 20 from the battery 30 and the capacitor 40 in order to prevent the regenerative electric power from being supplied to the battery 30 and the capacitor 40.

On the other hand, when it is determined from the obtained acceleration component value that the user performs an action of standing up, the process proceeds to step S106. In step S106, the controller 80 switches the mode to the operation mode and obtains the capacitor voltage value from the voltmeter 60, which measures the voltage of the capacitor 40.

When the obtained capacitor voltage value is greater than or equal to the predetermined value (Yes in step S107), the process proceeds to step S108 in which the controller 80 performs switching so as to supply the regenerative electric power, stored in the capacitor 40, to the motor 20 and performs control. For example, the controller 80 couples the motor 20 and the capacitor 40 in order to supply the regenerative electric power, stored in the capacitor 40, to the motor 20 and decouples the capacitor 40 from the battery 30 and the load 50 in order to prevent the regenerative electric power stored in the capacitor 40 from being supplied to the battery 30 and the load 50.

In this case, when the regenerative electric power stored in the capacitor 40 is supplied to the motor 20, the capacitance of the capacitor 40 becomes zero, and then electric power for outputting power of the motor 20 is required (Yes in step S109), the process proceeds to step S110. In step S110, the controller 80 performs switching so as to supply the battery electric power from the battery 30 to the motor 20. For example, the controller 80 couples the motor 20 and the battery 30 in order to supply the battery electric power from the battery 30 to the motor 20 and decouples the battery 30 from the capacitor 40 and the load 50 so as to prevent the battery electric power from being supplied to the capacitor 40 and the load 50.

When the obtained capacitor voltage value is smaller than the predetermined value (No in step S107), the process proceeds to step S110 described above.

<Modifications>

Although a preferred embodiment of the present disclosure has been described above, the present disclosure is not limited to the above-described embodiment and it is apparent to those skilled in the art that various modifications, additions, and omissions can be made thereto without departing from the spirit and scope recited in the claims.

Although an example in which the single power apparatus 100 operates in the operation mode and the recovery mode has been described in the above embodiment, the present disclosure is not limited thereto. For example, the disclosure can also be applied to a power system in which a first power apparatus for generating regenerative electric power in the recovery mode and a second power apparatus for outputting power to the moving device in the operation mode are separated from each other.

Figure 7:
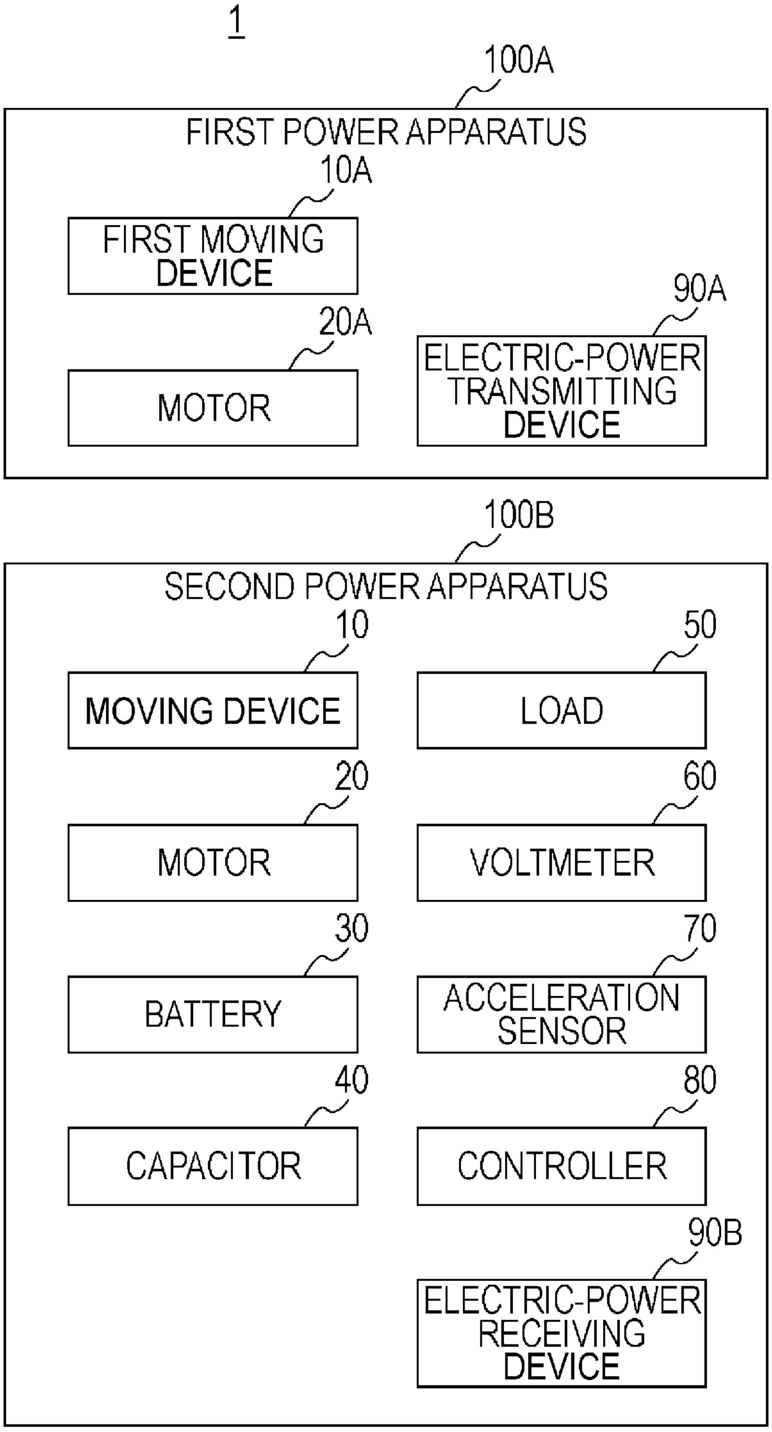
FIG. 7 is a block diagram showing a schematic configuration of a power system according to the present embodiment.

FIG. 7 is a block diagram showing a schematic configuration of a power system 1 according to the present embodiment. As shown in FIG. 7, the power system 1 includes a first power apparatus 100A and a second power apparatus 1008. The first power apparatus 100A has first moving device 10A, a motor 20A, and electric-power transmitting device 90A. The first moving device 10A moves in accordance with an action direction of a body part. The motor 20A recovers power generated by the movement of the first moving device 10A during action of the body part. The electric-power transmitting device 90A transmits the regenerative electric power, generated by the recovery of the power, to the second power apparatus 100B. The second power apparatus 100B has electric-power receiving device 90B in addition to elements that are similar to those in the power apparatus 100 according to the above-described embodiment. The electric-power receiving device 90B receives the transmitted regenerative electric power. A capacitor 40 in the second power apparatus 100B may be provided in the first power apparatus 100A or may be provided in each of the first power apparatus 100A and the second power apparatus 100B.

Figure 8:
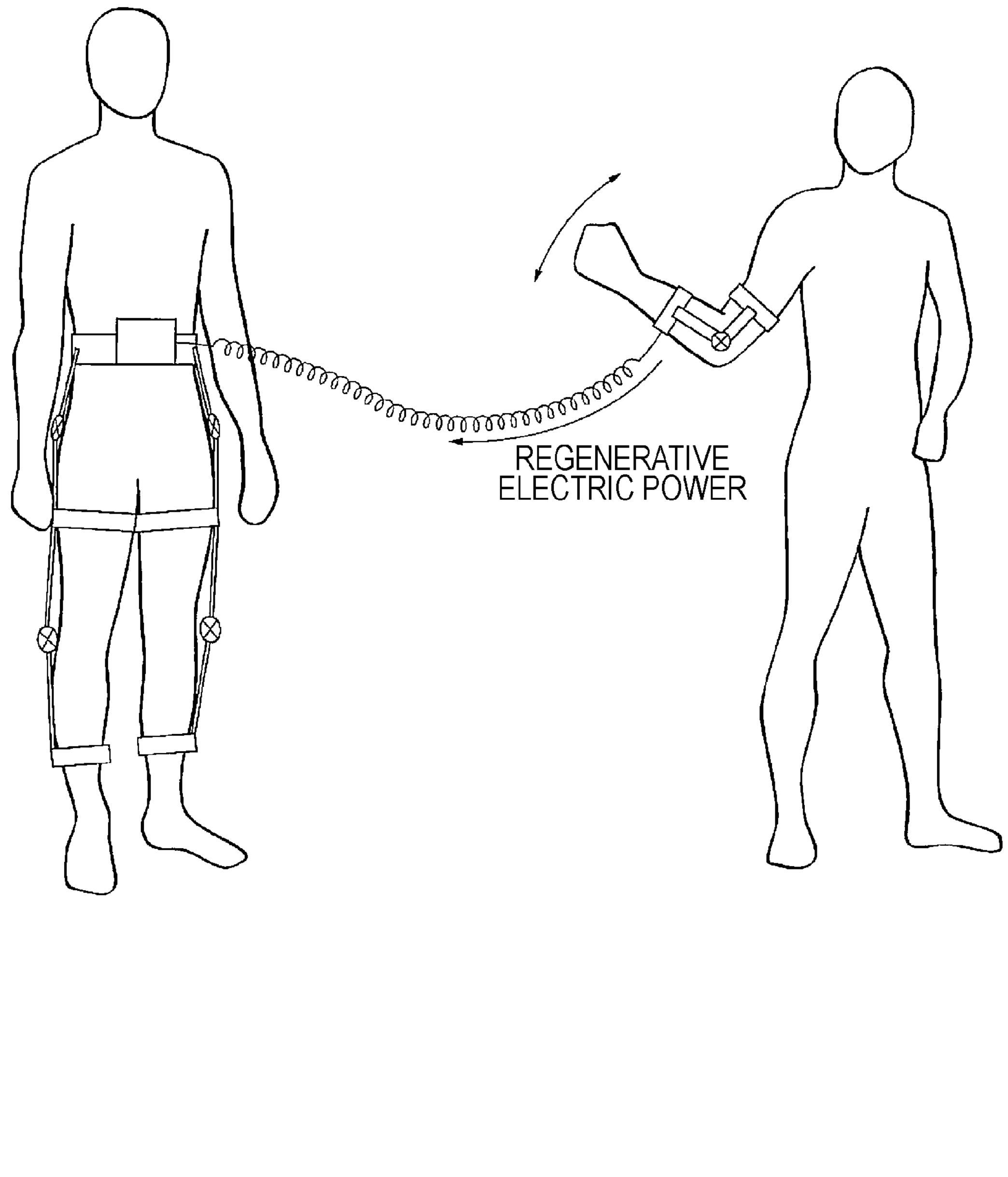
FIG. 8 is a schematic view showing the power system according to the present embodiment.

According to the power system 1 of the present embodiment, for example, as shown in FIG. 8, the arrangement may be such that a non-disabled person wears the first power apparatus 100A and a disabled person wears the second power apparatus 100B so as to allow electric power to be supplied to the second power apparatus 100B of the disabled person in accordance with an action of the non-disabled person. In addition, for example, the arrangement may also be such that, when a disabled person has a disability in his/her only leg, the first power apparatus 100A is attached to his/her non-disabled hand or arm and the power apparatus 100B is attached to his/her disabled leg. This arrangement allows electric power to be supplied to the second power apparatus 100B, attached to the disabled leg, in accordance with action of the non-disabled hand or arm.

Although a case in which the battery 30 and the single capacitor 40 are used as electric power sources has been described in the above embodiment, the battery 30 and multiple capacitors 40 may also be used as electric power sources. For example, when two capacitors 40 are used, control for performing alternately switching may be executed such that one of the capacitors 40 stores the regenerative electric power and the other capacitor 40 supplies the stored regenerative electric power to the battery 30. Such an arrangement makes it possible to continuously store the electric power.

Although a case in which both the battery 30 and the capacitor 40 are used as electric power sources has been described in the above embodiment, only the capacitor 40 may also be used as an electric power source. In such a case, for example, using multiple capacitors and controlling coupling between the multiple capacitors and the motor 20 makes it possible to provide a power apparatus corresponding to the output of the motor 20 and the amount of power recovered.

Although the description in the above embodiment has been given of a case in which the disclosed power apparatus 100 has the controlling device for automatically controlling switching between the first mode in which the motor outputs power to the moving device and the second mode in which the power of the motor is recovered, the power apparatus 100 is not limited thereto. For example, the power apparatus 100 may have switching device, such as a switch, for allowing a user to manually switch between the first mode and the second mode.

In addition, in the above-described embodiment, when the regenerative electric power that is greater than or equal to a predetermined value is stored in the capacitor 40, the battery electric power supplied from the battery 30 to the motor 20 is interrupted and the regenerative electric power is supplied from the capacitor 40 to the motor 20. However, the disclosed power apparatus 100 is not limited to the configuration, and may have a configuration in which the regenerative electric power is supplied, as needed, from the capacitor 40 to the motor 20. For example, the arrangement may be such that, when the power apparatus 100 instantaneously outputs high power, the regenerative electric power stored in the capacitor 40 is supplied to the motor 20.

Although a case in which the acceleration sensor 70 is used has been described in the above embodiment, the disclosed power apparatus 100 is not limited thereto. For example, an electromyograph (a myoelectric potential sensor) for measuring a myoelectric potential of a body part may be used. In such a case, the controller 80 switches the mode to the first mode, when the measured myoelectric potential is a potential corresponding to an action in the first action direction, and switches the mode to the second mode, when the measured myoelectric potential is a potential corresponding to an action in the second action direction, to perform control. This arrangement makes it possible to perform control according to the user's action and allows the user to use the power apparatus 100 without a sense of discomfort. In addition, for example, an external sensor may also be used in addition to the sensor, such as the acceleration sensor or the electromyograph, attached to the power apparatus 100 or the user. One example of the external sensor is image-capturing device for capturing an image of the user's action and analyzing the image.

Although a recovery load of the motor in the recovery mode has not been described in the above embodiment, the recovery load of the motor may be controlled in accordance with, for example, an action of a body part of interest. More specifically, for example, the recovery load of the motor is controlled such that the muscle power of the user's both thighs and so on, the muscle power being required to support the body, does not have to be used when the user performs an action of slowly sitting down. The recovery load acts as power in a direction opposite to the direction of the user's action of sitting down. Thus, if the amount of recovery load is too small, muscle power for supporting the body is required, and conversely, if the amount of recovery load is too large, the user needs to sit down against the recovery load and thus muscle power therefor is required. Accordingly, in the recovery mode, the recovery load is adjusted and controlled such that no muscle power is required. For example, an electromyograph for measuring a myoelectric potential of a body part of interest can be used to control the recovery load of the motor such that no myoelectric potential is generated (i.e., such that no muscle power is required).

What is claimed is:

1. A power apparatus comprising:

a moving device configured to move in accordance with an action of a body part;

a motor that outputs, during an action of the body part in a first action direction, power to the moving device so as to cause the moving device to move in the first action direction and that recovers, during an action of the body part in a second action direction, power generated by the movement of the moving device in the second action direction;

a capacitor that stores regenerative electric power generated by the recovery of the power and that supplies the stored regenerative electric power to the motor when the motor outputs the power to the moving device;

a battery that supplies battery electric power to the motor when the motor outputs the power to the moving device; and a controlling device configured to control switching between a first mode in which the motor outputs the power to the moving device and a second mode in which the power of the motor is recovered;

wherein, in the first mode, when the regenerative electric power stored in the capacitor is greater than or equal to a predetermined value, the controlling device performs control so as to block supply of the battery electric power from the battery to the motor and so as to supply the regenerative electric power from the capacitor to the motor, and when the regenerative electric power stored in the capacitor is smaller than the predetermined value, the controlling device performs control so as to supply the battery electric power from the battery to the motor, and wherein, when the moving device is not moving and the regenerative electric power is stored in the capacitor, the controlling device performs control so as to supply the regenerative electric power from the capacitor to the battery.

2. The power apparatus according to claim 1, wherein, in the second mode, the controlling device performs control so as to supply the regenerative electric power to the capacitor when a voltage value of the capacitor is not a maximum value and so as to supply the regenerative electric power to a load when the voltage value of the capacitor is the maximum value.

3. The power apparatus according to claim 1, further comprising an acceleration sensor that measures acceleration of the action of the body part, wherein, when the measured acceleration contains a component in a direction opposite to a direction of gravity, the controlling device switches a mode to the first mode to perform control, and when the measured acceleration contains a component in the direction of gravity, the controlling device switches a mode to the second mode to perform control.

4. The power apparatus according to claim 1, further comprising an electromyograph that measures a myoelectric potential of the body part, wherein, in the second mode, the controlling device controls a recovery load of the motor in accordance with the measured myoelectric potential so that no myoelectric potential is generated.

5. The power apparatus according to claim 1, further comprising an electromyograph that measures a myoelectric potential of the body part, wherein, when the measured myoelectric potential is a potential corresponding to an action in the first action direction, the controlling device switches a mode to the first mode to perform control, and when the measured myoelectric potential is a potential corresponding to an action in the second action direction, the controlling device switches a mode to the second mode to perform control.

6. The power apparatus according to claim 1, comprising a plurality of capacitors, wherein the controlling device performs control so as to alternately switch one of the plurality of capacitors that stores the regenerative electric power to/from another one of the capacitors that supplies the stored regenerative electric power to the battery.

7. A power control method for controlling the power apparatus according to claim 1, the power control method comprising:

causing the motor to receive, during an action of the body part in the first action direction, the regenerative electric power supplied from the capacitor and to output the power to the moving device;

causing the motor to recover, during an action of the body part in the second action direction, the power generated by movement of the moving device in the second action direction and causing the capacitor to store regenerative electric power generated by the recovery of the power; and supplying, when the moving device is not moving and the regenerative electric power is stored in the capacitor, the regenerative electric power from the capacitor to the battery.

8. A power system comprising:

a first power apparatus; and a second power apparatus, wherein the first power apparatus has:

a first moving device configured to move in accordance with a direction of an action of a first body part, a first motor that recovers power generated by the movement of the first moving device during the action of the first body part, and an electric-power transmitting device configured to transmit regenerative electric power generated by the recovery of the power to the second power apparatus, wherein the second power apparatus has:

a second moving device configured to move in accordance with a direction of an action of a second body part, a second motor that outputs, during an action of the second body part in a first action direction, power to the second moving device so as to cause the second moving device to move in the first action direction and that recovers, during an action of the second body part in a second action direction, power generated by the movement of the second moving device in the second action direction, an electric-power receiving device configured to receive the regenerative electric power transmitted from the electric-power transmitting device, a capacitor that stores regenerative electric power generated by the recovery of the power and the above received regenerative electric power and that supplies the stored regenerative electric power to the second motor when the second motor outputs the power to the second moving device, a battery that supplies battery electric power to the second motor when the second motor outputs the power to the second moving device, and a controlling device configured to control switching between a first mode in which the second motor outputs the power to the second moving device and a second mode in which the power of the motor is recovered, wherein, in the first mode, when the regenerative electric power stored in the capacitor is greater than or equal to a predetermined value, the controlling device performs control so as to block supply of the battery electric power from the battery to the second motor and so as to supply the regenerative electric power from the capacitor to the second motor, and when the regenerative electric power stored in the capacitor is smaller than the predetermined value, the controlling device performs control so as to supply the battery electric power from the battery to the second motor, and wherein, when the second moving device is not moving and the regenerative electric power is stored in the capacitor, the controlling device performs control so as to supply the regenerative electric power from the capacitor to the battery.

* * * * *

UNITED STATES PATENT AND TRADEMARK OFFICE

CERTIFICATE OF CORRECTION

PATENT NO. : 7,981,061 B2
APPLICATION NO. : 12/778352
DATED : July 19, 2011
INVENTOR(S) : Kusuura It is certified that error appears in the above-identified patent and that said Letters Patent is hereby corrected as shown below:

In Column 3, Line 28, delete "DESCRIPTION" and insert -- DETAILED DESCRIPTION --, therefor.

In Column 8, Line 20, delete "1008." and insert -- 100B. --, therefor.

Signed and Sealed this
Twenty-sixth Day of June, 2012

David J. Kappos
*Director of the United States Patent and Trademark Office*